United States Patent [19]

Abrahamson

[11] Patent Number: 5,403,291

[45] Date of Patent: Apr. 4, 1995

[54] CATHETER WITH ELONGATED SIDE HOLES

[75] Inventor: Timothy A. Abrahamson, Seattle, Wash.

[73] Assignee: Quinton Instrument Company, Bothell, Wash.

[21] Appl. No.: 101,520

[22] Filed: Aug. 2, 1993

[51] Int. Cl.⁶ .......................................... A61M 25/00
[52] U.S. Cl. ................................ 604/280; 128/658; 604/43; 604/264; 604/281; 604/282
[58] Field of Search ................ 604/43, 264, 280–282; 128/658

[56] References Cited

U.S. PATENT DOCUMENTS

| | | | |
|---|---|---|---|
| Re. 31,873 | 4/1985 | Howes | 128/674 |
| 390,177 | 9/1888 | Lee . | |
| 1,045,326 | 11/1912 | Ruflin . | |
| 1,922,084 | 8/1933 | Gerow . | |
| 2,173,527 | 9/1939 | Agayoff | 604/282 |
| 2,175,726 | 10/1939 | Gebauer . | |
| 2,819,718 | 1/1958 | Goldman . | |
| 2,936,761 | 5/1960 | Snyder | 604/282 |
| 3,042,045 | 7/1962 | Sheridan . | |
| 3,314,430 | 4/1967 | Alley et al. . | |
| 3,359,974 | 12/1967 | Khalil . | |
| 3,394,705 | 7/1968 | Abramson . | |
| 3,437,088 | 4/1969 | Bielinski . | |
| 3,448,739 | 6/1969 | Stark et al. . | |
| 3,452,756 | 7/1969 | Harautuneian . | |
| 3,459,188 | 8/1969 | Roberts . | |
| 3,550,591 | 12/1970 | MacGregor . | |
| 3,556,161 | 1/1971 | Roberts | 138/141 |
| 3,566,874 | 3/1971 | Shepherd et al. . | |
| 3,593,713 | 7/1971 | Bogoff et al. . | |
| 3,599,620 | 8/1971 | Balin . | |
| 3,612,050 | 10/1971 | Sheridan . | |
| 3,726,281 | 4/1973 | Norton et al. . | |
| 3,746,003 | 7/1973 | Blake et al. . | |
| 3,799,172 | 3/1974 | Szpur . | |
| 3,828,767 | 8/1974 | Spiroff . | |
| 3,875,938 | 4/1975 | Mellor . | |
| 3,896,815 | 7/1975 | Fettel et al. . | |
| 3,995,623 | 12/1976 | Blake et al. . | |
| 4,004,588 | 1/1977 | Alexander . | |
| 4,100,246 | 7/1978 | Frisch . | |
| 4,134,402 | 1/1979 | Mahurkar . | |
| 4,144,884 | 3/1979 | Tersteegen et al. . | |
| 4,168,703 | 9/1979 | Kenigsberg . | |
| 4,180,068 | 12/1979 | Jacobsen et al. . | |
| 4,202,332 | 5/1980 | Tersteegen et al. . | |
| 4,217,895 | 8/1980 | Sagae et al. . | |
| 4,257,416 | 3/1981 | Prager . | |
| 4,270,535 | 6/1981 | Bogue et al. . | |
| 4,276,880 | 7/1981 | Malmin | 604/264 |
| 4,327,722 | 5/1982 | Groshong et al. . | |
| 4,385,631 | 5/1983 | Uthmann | 604/284 |
| 4,403,983 | 9/1983 | Edelman et al. | 604/43 |
| 4,406,656 | 9/1983 | Hattler et al. | 604/280 |
| 4,431,426 | 2/1984 | Groshong et al. . | |
| 4,443,333 | 4/1984 | Mahurkar | 210/87 |
| 4,451,252 | 5/1984 | Martin | 604/43 |
| 4,465,482 | 8/1984 | Tihel | 604/280 |
| 4,484,585 | 11/1984 | Baier . | |
| 4,493,696 | 1/1985 | Uldall | 604/43 |
| 4,543,087 | 9/1985 | Sommercorn et al. | 604/43 |

(List continued on next page.)

FOREIGN PATENT DOCUMENTS

| | | | |
|---|---|---|---|
| 1092927 | 1/1981 | Canada | 604/43 |
| 1150122 | 7/1983 | Canada . | |
| 0036642 | 9/1981 | European Pat. Off. | 604/43 |
| 0079719 | 5/1983 | European Pat. Off. . | |
| 0333308 | 9/1989 | European Pat. Off. . | |
| 8404043 | 10/1984 | WIPO . | |
| 8404664 | 12/1984 | WIPO . | |

*Primary Examiner*—C. Fred Rosenbaum
*Assistant Examiner*—Bryan Leander Tsosie
*Attorney, Agent, or Firm*—Andrew J. Beck; Montgomery W. Smith; Richard D. Allison

[57] ABSTRACT

An elongate catheter having one or more lumens therein and at least one lumen in flow communication with a side opening in the sidewall of the catheter wherein the side opening includes first and second sides and generally parallel distal and proximal ends thereon to form a generally slot-shaped side opening, and the opening is oriented diagonally with respect to the longitudinal axis of the catheter.

28 Claims, 4 Drawing Sheets

U.S. PATENT DOCUMENTS

| | | | |
|---|---|---|---|
| 4,547,193 | 10/1985 | Rydell | 604/282 |
| 4,549,879 | 10/1985 | Groshong et al. | |
| 4,559,046 | 12/1985 | Groshong et al. | |
| 4,568,329 | 2/1986 | Mahurkar | 604/43 |
| 4,583,968 | 4/1986 | Mahurkar | 604/43 |
| 4,619,643 | 10/1986 | Bai | 604/43 |
| 4,623,327 | 11/1986 | Mahurkar | 604/4 |
| 4,626,240 | 12/1986 | Edelman et al. | 604/43 |
| 4,643,711 | 2/1987 | Bates | 604/43 |
| 4,661,110 | 4/1987 | Fortier et al. | 604/256 |
| 4,682,978 | 7/1987 | Martin | 604/43 |
| 4,692,141 | 9/1987 | Mahurkar | 604/43 |
| 4,753,640 | 6/1988 | Nichols et al. | 604/247 |
| 4,756,303 | 7/1988 | Kawashima et al. | 128/6 |
| 4,772,268 | 9/1988 | Bates | 604/174 |
| 4,795,439 | 1/1989 | Guest | 604/280 |
| 4,813,429 | 3/1989 | Eshel et al. | 604/43 |
| 4,822,345 | 4/1989 | Danforth | 604/282 |
| 4,863,441 | 9/1989 | Lindsay et al. | 604/264 |
| 4,894,057 | 1/1990 | Howes | 604/280 |
| 4,898,591 | 2/1990 | Jang et al. | 604/282 |
| 4,934,340 | 6/1990 | Ebling et al. | 128/6 |
| 4,995,865 | 2/1991 | Gahara et al. | 604/43 |
| 5,004,455 | 4/1991 | Greenwood et al. | 604/43 |
| 5,019,057 | 5/1991 | Truckai | 604/282 |
| 5,057,073 | 10/1991 | Martin | 604/43 |
| 5,171,216 | 12/1992 | Dasse et al. | 604/43 |
| 5,188,592 | 2/1993 | Hakki | 604/43 |
| 5,201,723 | 4/1993 | Quinn | 604/264 |
| 5,221,255 | 6/1993 | Mahurkar et al. | 604/43 |
| 5,221,256 | 6/1993 | Mahurkar | 604/43 |

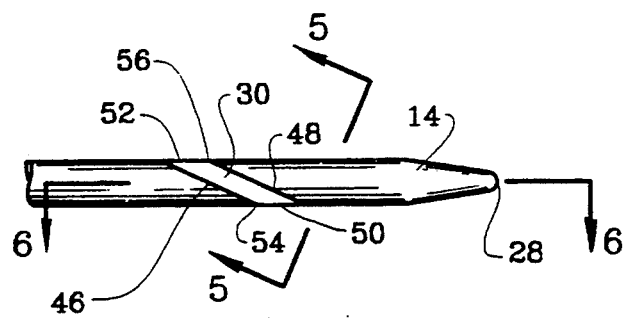
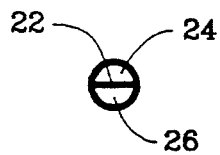
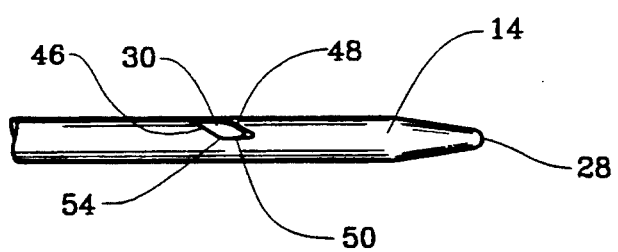
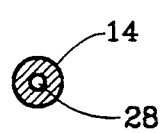
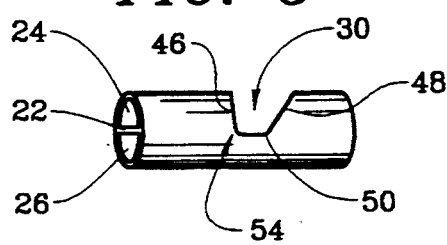
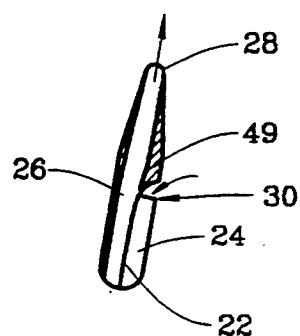

CATHETER WITH ELONGATED SIDE HOLES

FIELD OF THE INVENTION

The present invention relates to catheters and more particularly to a catheter having one or more lumens therein and an elongated and generally slot-shaped side hole extending through the sidewall of the catheter.

BACKGROUND OF THE INVENTION

Single or multiple lumen catheters are well known in the medical field and are widely used in medical procedures such as hemodialysis or other procedures wherein it is desirable to inject or remove fluids through one or more lumens of the catheter. For example, in hemodialysis it is desirable to introduce blood into a vein or other vessel of a patient through a first lumen while simultaneously removing a corresponding amount of blood from the patient through a second lumen of the catheter. In certain situations, it may also be desirable to have a third lumen extending through the catheter to allow a medication to be injected therethrough without interfering with the operation of the first or second lumens.

The currently available single or multiple lumen catheters frequently have an opening at the distal end thereof and one or more openings or holes along the sidewall of the catheter. During hemodialysis, the arterial or intake lumen is used to remove blood from the patient. This intake lumen typically opens along the sidewall of the catheter. In use, the side opening may occasionally become completely or partially occluded by the interior wall of the patient's blood vessel when the catheter has been inserted. The complete or partial occlusion of the side opening will significantly reduce the flow of blood through the intake lumen of the catheter and may also damage the interior wall of the patient's blood vessel.

In certain commercially available catheters one or more relatively large side openings are used. With these side openings it is typically recommended that the flow of fluid through the side opening be checked prior to hemodialysis. If the side opening is occluded, it is recommended that the catheter be rotated or otherwise repositioned. A further difficulty with the use of the large single side opening is that the side opening may occasionally get caught on the tissue or the wall of the blood vessel along the incision during insertion. Yet another difficulty with the use of a large single side opening is that the catheter may kink or bend at the side opening during insertion if the catheter tip meets resistance during insertion because the large side opening may weaken the column strength of the catheter.

In other commercially available catheters, as disclosed in U.S. Pat. No. 4,543,087 granted to Sommercorn et al., a plurality of spaced apart side openings are provided so that even if one side opening is occluded at least one of the remaining side openings may remain open. Another approach to solving the problem of occlusion is disclosed in U.S. Pat. No. 4,795,439 granted to Guest. In this patent, the lumens of the distal portion of the catheter are twisted such that the plurality of side openings in the catheter are not aligned in a straight line along the distal portion of the catheter.

The use of multiple side openings in a catheter provides an increased likelihood that a clot may form along or in one or more of the side openings as compared to the likelihood of clotting in catheters with a single side opening for each lumen. This increased likelihood of clot formation is believed to be caused, at least partially, by the presence of multiple surfaces between each of the side openings which may provide an area of reduced flow in the lumen which allows the clot to form thereon. Additionally, it is a common practice to perform a heparin flush of the catheter periodically to decrease the likelihood of clot formation on the catheter. The heparin flush technique is believed to be less effective in removing or preventing clot formation in catheters with multiple side openings because if one of the side openings is occluded by a clot, the heparin will merely flow through the side opening which provides the least resistance. There is also the possibility that the heparin may be washed out of the distal portion of the lumen of the catheter by blood which may enter one or more of the proximally located side openings to flush the heparin through the lumen and out of the catheter through one or more of the distally located side openings.

One final approach to solving the problem of preventing occlusion and clot formation involves the use of elongate slits as side openings in the catheter. The slits completely close the lumen between uses and are opened only upon the application of either positive or negative pressure to the fluid in the lumen of the catheter. One difficulty with this approach is that it requires increased pressure through the lumens of the catheter to open the slit openings during use. Additionally, if the blood is not completely removed from the lumen by the heparin flush, the stagnant flow of fluid in the lumen may result in the formation of a clot in the lumen which will be difficult to remove through the slit.

The present invention overcomes the disadvantages described above by providing an elongated side opening which is preferably oriented diagonally along the distal portion of the catheter to retain the column strength of the catheter while minimizing the likelihood of occlusion or clot formation.

SUMMARY OF THE PRESENT INVENTION

The present invention is directed to a generally slot-shaped side opening for use on a catheter having one or more lumens therein. In a preferred form of the present invention, the side opening is preferably oriented diagonally along the longitudinal axis of the catheter such that one end of the slot is oriented distally of the other end of the slot. The end of the slot preferably terminates adjacent to the sides of the respective surface of the lumen to maximize the open passageway for the flow of fluid therethrough. Additionally, the sidewalls of the side opening are preferably spaced apart and generally parallel to each other to form an elongated and diagonally oriented slot which extends around a significant portion of the diameter of the catheter.

The present invention generally includes an elongate catheter having:
- an elongate body portion formed by a circumferential sidewall and having a longitudinal axis and distal and proximal end portions thereon;
- a first lumen in said body portion extending between said proximal end portion and a side opening formed in said sidewall of said body portion;
- said side opening including first and second sides thereon wherein said first side is formed proximally of said second side on said sidewall; and
- the side opening further includes a plurality of spaced apart ends extending between said first and second sides such that at least one of said first and second sides is oriented diagonally with respect to said longitudinal axis of said body portion.

The catheter of the present invention may further include spaced apart ends which include distal and proximal wall portions thereon, and the intersection of said distal wall portion and second side of said side opening is located distally of the intersection of said proximal wall portion and said first side of said side opening or spaced apart ends which include distal and proximal wall portions thereon, and the intersection of said distal wall portion and said first side of said side opening is located distally of the intersection of said proximal wall portion and said first side of said side opening.

The preferred form of the catheter of the present invention is a dual or triple lumen hemodialysis catheter having at least one generally D-shaped lumen therein. The catheter preferably includes a blood return or first lumen which extends between the proximal end of the catheter and the distal opening on the catheter tip which is located at the distal end of the catheter. The intake or second lumen of the catheter preferably extends between the proximal end of the catheter and a side opening which is preferably located along the distal portion of the catheter and generally proximal to the catheter tip.

An object of the present invention is to provide a side opening in the sidewall of a catheter which is shaped and oriented to minimize the kinking of the catheter at the side opening during insertion.

Another object of the present invention is to provide a side opening in the sidewall of a catheter which is shaped and oriented to minimize tunnel tract tissue snag and blood vessel wall snag during the insertion or removal of the catheter.

Another object of the present invention is to prevent clotting by providing a side opening in the sidewall of a catheter which is shaped and oriented to be essentially self flushing such that external fluid flow may pass directly from the proximal side of the side opening to the distal side of the side opening without interruption.

Yet another object of the present invention is to reduce vessel wall occlusion by providing a side opening which maximizes the open passageway for fluid flow even when a portion of the slot is occluded by or sucked against a portion of the vessel wall.

BRIEF DESCRIPTION OF THE DRAWINGS

FIG. 2 is an enlarged elevated front side view of the distal portion of the embodiment shown in FIG. 1;

FIG. 3 is an enlarged right side view of the distal portion of the embodiment shown in FIG. 1;

FIG. 5 is an enlarged diagrammatic right side view of the distal portion of the embodiment shown in FIG. 1, taken generally along lines 5—5 of FIG. 2A showing an end view of the side opening of the present invention.

FIG. 6 is an enlarged cross-sectional view of the distal portion of the embodiment shown in FIG. 1, taken generally along lines 6—6 of FIG. 2A;

FIG. 7 is a cross-sectional view of the embodiment shown in FIG. 1 taken generally along lines 7—7 of FIG. 1;

FIG. 8 is a cross-sectional view of the embodiment shown in FIG. 1 taken generally along lines 8—8 of FIG. 1;

DESCRIPTION OF THE PREFERRED EMBODIMENTS

Figure 1:
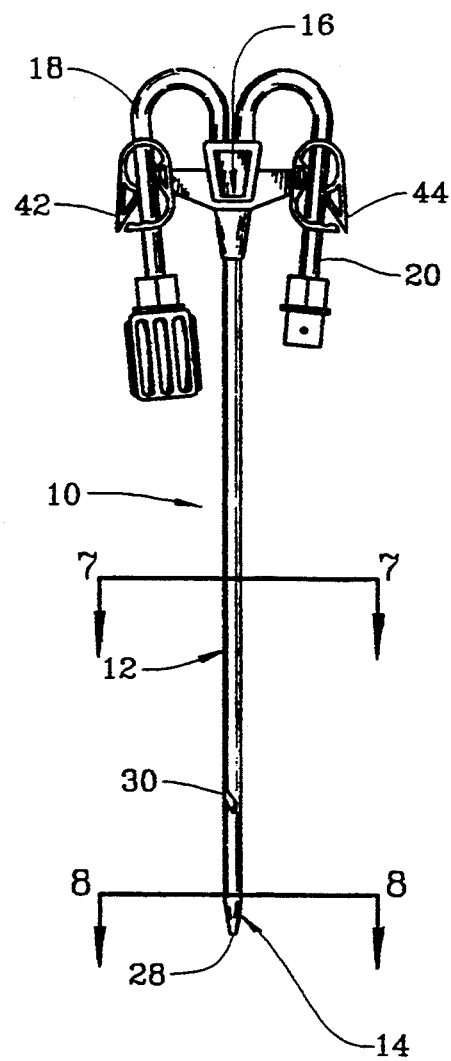
FIG. 1 is an elevated left side view of a catheter of the present invention.

As shown in the drawings, the preferred form of the overall catheter assembly 10 of the present invention is generally similar to the dual lumen hemodialysis catheter shown in U.S. Pat. No. 4,583,968 granted to Mahurkar on Apr. 22, 1986. The catheter assembly 10 generally includes an elongate and slightly oval-shaped body portion 12 having a tip member 14 on the distal end thereof and a Y-shaped connector hub 16 on the proximal end thereof. As shown in FIG. 1, the proximal end of the Y-connector includes extension members 18 and 20 thereon. As used herein, the term "proximal" is intended to refer to the end or portion of a member which is normally oriented or positioned away from the patient while the term "distal" refers to the end or portion of a member in use which is nearest to the patient. Although the preferred form of the present invention is described herein with respect to multiple lumen catheters, it is intended that the present invention may also be used with nearly any catheter having one of more lumens therein including angiographic or various diagnostic catheters.

The body portion 12 of the preferred embodiment of the catheter assembly 10 is hollow except for a generally flat, longitudinal septum 22 which divides the interior of the hollow cylinder into two preferably parallel lumens 24 and 26, with each lumen, 24 and 26, having a generally D-shaped cross section as shown in FIG. 7. As illustrated by the arrows in FIG. 6, the lumen 24 is the blood intake or arterial lumen, and the lumen 26 is the blood return or venous lumen.

At the distal end of the catheter assembly 10, the exterior surface of the body portion 12 merges into the smoothly tapered conical tip member 14. On the inside of the body portion 12, the blood return lumen 26 extends longitudinally all the way through the tip member 14, bending slightly as it passes through the tip member 14 so that it opens at distal opening 28 near the center of the distal end of the tip member as can be seen in FIG. 6. Within the tip member 14 the preferred cross-sectional shape of the lumen 26 gradually changes from D-shaped at the proximal end of the tip member 14 to circular at the distal end of the tip member 14 at the distal opening 28 as shown in FIGS. 7 and 8. The cross-sectional diameter of the distal opening 28 is preferably maximized so that the blood return lumen 26 may not require a side opening therein. In order to provide longitudinal spacing between the distal openings of the two lumens 24 and 26, the blood intake lumen 24 is terminated at side opening 30 in the sidewall of the catheter as described more fully below.

At the proximal end of the catheter 10, the two D-shaped lumens 24 and 26 connect to a Y-shaped connector hub 16 which forms two internal passageways communicating with the proximal ends of the catheter lumens 24 and 26. The passageways of the connector hub 16 diverge from each other and assume a circular cross section as they extend toward the proximal end of the connector hub 16. The passageways may also increase in cross-sectional area as they extend toward the proximal end of the connector hub 16. The connector hub 16 is preferably molded in place on the end of the catheter, using mold core pins to form the hub passageways. Alternatively, the walls of the catheter lumens 24 and 26 may be expanded at the proximal end of the body portion 12 of the catheter to fit over the corresponding portions of a preformed connector hub 16 with the inside walls of the catheter lumens 24 and 26 being bonded to the mating walls of the connector hub 16.

To facilitate connection of the connector hub 16 to the conventional tubes leading to a dialysis unit, and also to accommodate a pair of clamps 42 and 44 for opening and closing the blood intake and return lumens 24 and 26, the connector hub 16 is fixedly attached to the pair of tubular extension members 18 and 20 as shown in FIG. 1. These extension members 18 and 20 are relatively soft and flexible so that they may be manipulated as needed and also easily closed by the pressure of the clamps 42 and 44. As shown in FIG. 1, the preferred form of the extension members 18 and 20 is pre-curved or bent to facilitate the positioning of the extension members 18 and 20 along the body of the patient when the catheter assembly 10 is inserted therein. The clamps 42 and 44 serve as on-off valves for controlling the flow of blood between the catheter assembly 10 and the dialysis unit. At the proximal end of the extension members 18 and 20, a pair of luer connectors are formed or bonded as integral parts thereof. The luer connectors serve as a means for coupling the proximal ends of the extension members 18 and 20 to a plurality of flexible tubes (not shown) which lead to the extracorporeal or hemodialysis treatment unit.

As shown in FIGS. 2A and 3–5, the preferred embodiment of the present invention includes a generally elongated and diagonally oriented side opening 30 formed in the sidewall of the catheter. Although the side opening 30 is preferably laser cut into the sidewall of the catheter, it is anticipated that it may be formed in the sidewall of the catheter by various other currently available methods.

Figure 2B:
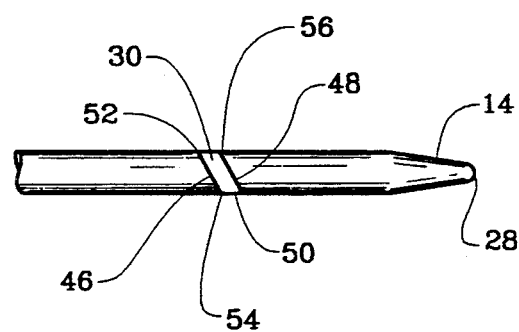
FIG. 2B is an enlarged elevated front side view of an alternate embodiment of the distal portion of the embodiment shown in FIG. 1.
Figure 12:
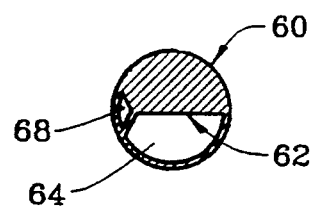
FIG. 12 is an enlarged cross-sectional view of the embodiment shown in FIG. 9 taken along lines 12—12 of FIG. 10.
Figure 13:
FIG. 13 is an enlarged end view of the catheter shown in FIG. 9 taken generally along lines 13—13 of FIG. 10.

FIG. 2B shows an alternate form of the present invention where like numbers have been added to like members.

As shown in FIG. 2A, the side opening 30 is preferably formed as a slot-shaped opening having a first side 46 which is positioned proximally of a second side 48 such that the side opening 30 is not perpendicular to the longitudinal axis of the catheter. In the preferred form of the present embodiment, the side opening 30 is oriented at an angle of about 30 degrees with respect to the longitudinal axis of the catheter although it is anticipated that this could be nearly any angle including a side opening wherein the sides and ends of the side opening 30 are not parallel with respect to each other. Additionally, the first and second sides 46 and 48 are preferably formed to end generally at the surface of the septum 22 so that the cross-sectional area of the side opening 30 is maximized. The side opening 30 also includes distal and proximal ends 50 and 52, respectively, which are spaced apart from each other a predetermined distance as shown in FIG. 2. The distance between the distal and proximal ends, 52 and 54, is dependent on a number of factors including the overall diameter of the catheter, the number of lumens in the catheter and its intended use. The first and second sides 46 and 48 and the distal and proximal ends 50 and 52 of the side opening 30 are preferably oriented along the sidewall of the catheter such that the tissue along the incision as well as the wall of the blood vessel are supported by at least one of the distal or proximal sides 46 and 48 of the side opening 30 during the insertion or removal of the catheter, as best shown in FIG. 3. This minimizes the depth with which the tissue or blood vessel wall is able to enter the side opening 30 thereby minimizing the likelihood that the catheter will be caught on or otherwise will be hung up on the tissue or blood vessel wall during the insertion of the catheter.

Figure 4:
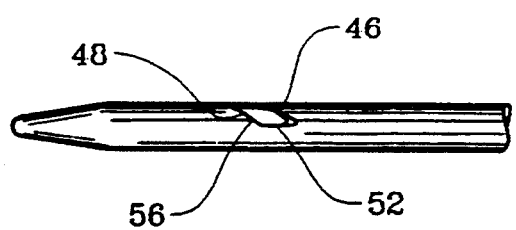
FIG. 4 is an enlarged left side view of the distal portion of the embodiment shown in FIG. 1.

As shown in FIG. 3, it is also preferred that the angle 54 formed by intersection of the first side 46 and the distal end 50 of the side opening 30 is relatively shallow. Additionally, as shown in FIG. 4, the angle 56 formed by the intersection of the second side 48 and the proximal end 52 of the side opening 30 is also relatively shallow. Therefore, when the catheter is inserted into the patient, the tissue initially passes over the distal end 50 of the side opening 30 and contacts the intersection of the distal end 50 and the first side 46 and is lifted up or supported along the gradually inclined surface found on this portion of the side opening 30. Additionally, the physician may occasionally twist the catheter during insertion into the patient. With the preferred orientation of the side opening 30 of the present invention, the side opening 30 may essentially be threaded into the incision of the patient as the physician rotates the catheter along the orientation of the side opening 30 during the insertion procedure.

When the catheter is removed from the patient, the tissue initially passes over the proximal end 52 of the side opening 30 and contacts the intersection of the second side 48 and the proximal end 52 of the side opening 30 so that the tissue is lifted up or supported along the gradually inclined surface formed on this portion of the side opening 30. The incline angles of the side opening 30 are at least partially controlled by the slot angle and corner radius at the intersection of the distal and proximal ends 50 and 52 and the first and second sides 46 and 48, and an example of this is shown in FIG. 5.

Additionally, the spacing between the first and second sides 46 and 48 and the orientation of the side opening 30 along the catheter is optimized to yield the greatest tube stiffness in the slot area to minimize kinking and reduce the force necessary to insert or remove the catheter from the patient. The slot opening 30 is also shaped and oriented along the catheter to optimize the flow of fluid therethrough at a full range of flow rates and pressures while minimizing the likelihood of occlusion of the side opening 30 against the wall of the blood vessel. In the preferred embodiment of the present invention, the likelihood of complete occlusion of the side opening 30 by the wall of the blood vessel is minimized because the side opening extends along approximately one-half of the external surface or nearly 180 degrees of the circumference of the catheter so that, even if the side opening 30 were positioned against the wall of the blood vessel, it is unlikely that the entire side opening 30 will be occluded by the wall of the blood vessel.

As shown best in FIG. 6, the blood intake lumen 24 terminates at the side opening 30. The area of the catheter which is distal to the blood intake lumen 24 is preferably closed by a plug material 49, as shown in FIG. 6, which is molded as part of or inserted into the blood intake lumen 24 and is adhesively or otherwise fixedly connected to the distal end portion of the catheter. The plug material 49 preferably fits flush with the distal surface of the side opening 30 to prevent the formation of a reduced or stagnant flow area at the distal end of the intake lumen 24. Therefore, as the side opening 30 is flushed by the flow of blood passing between the proximal end 52 and distal end 50, the blood also contacts the smooth surface formed by the second side 48 and plug material 49. The tip member 14 may be a pre-formed member which may be made out of a variety of materials including polyurethane or polyvinyl chloride. FIGS. 7 and 8 are illustrative of the preferred shape of the blood return lumen 26 proximally and distally of the side opening 30.

Figure 9:
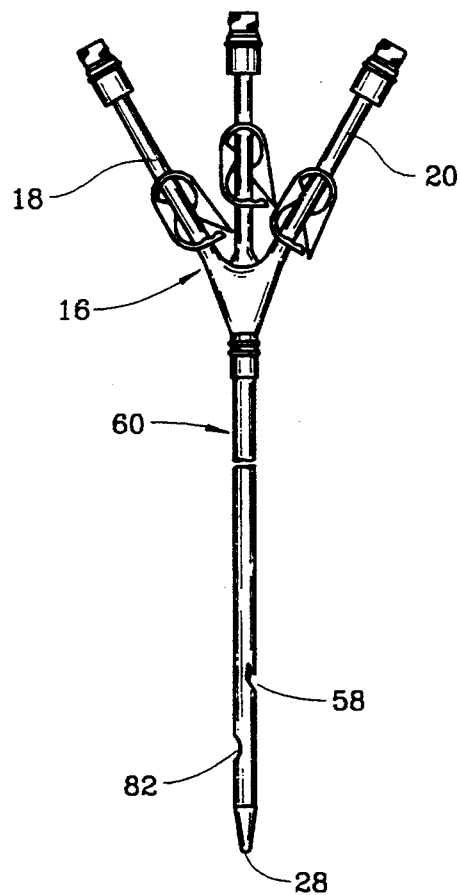
FIG. 9 is an elevated side view of a triple lumen catheter constructed in accordance with the present invention.
Figure 11:
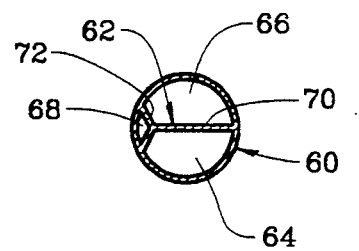
FIG. 11 is an enlarged cross-sectional view of the embodiment shown in FIG. 9 taken generally along lines 11—11 of FIG. 10.
Figure 10:
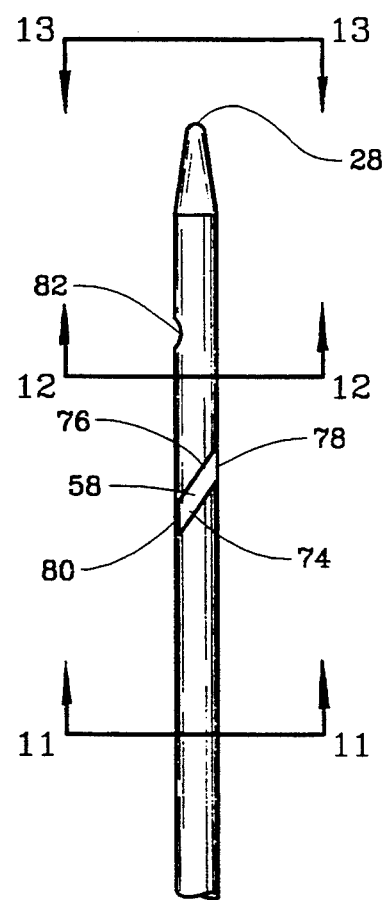
FIG. 10 is an enlarged elevated side view of the distal portion of the embodiment shown in FIG. 9.
Figure 14:
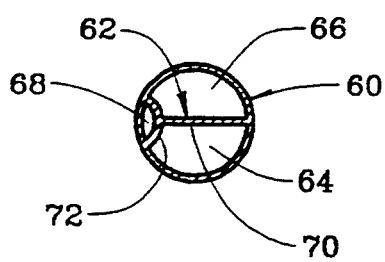
FIG. 14 is an enlarged cross-sectional view of an alternate form of a triple lumen catheter constructed in accordance with the present invention similar to the view shown in FIG. 11.

As shown in FIGS. 9–14, a side opening 58 in accordance with the present invention may also be used on triple lumen catheters; including a triple lumen catheter 60 of the type described herein. Like numbers have been added to like members which are more fully described above. In these embodiments the catheter includes a septum 62 which forms first, second and third lumens, 64, 66 and 68 respectively. If the catheter 60 is used for hemodialysis, the first and second lumens 64 and 66 preferably function similar to the blood return and blood intake lumens 26 and 24 of the embodiment described above. FIG. 9 shows the side opening 58 of the present embodiment in communication with the second lumen 66. As shown in FIGS. 11 and 14, the first and second lumens 64 and 66 are formed by first and second wall portions 70 and 72 of the septum 62. In these embodiments, the first wall portion 70 is generally straight and extends inwardly from the sidewall of the catheter 60. The second wall portion 72 is preferably bent (FIG. 11 or 14) such that the ends of the second wall portion 72 contact the sidewall of the catheter at an angle greater than or equal to ninety degrees to reduce the likelihood of a stagnant flow area within the first and second lumens 64 and 66 of the catheter 60.

The side opening 58 of this embodiment preferably extends about 160 degrees around the circumference of the catheter. The side opening 58 includes first and second sides 74 and 76 which are located adjacent to the intersection of the first and second wall portions 70 and 72 of the septum 62 and the sidewall of the catheter 60. As with the prior embodiment, the first side 74 is preferably located proximally of the second side 76 of the side opening 58 and is also spaced apart from the second side 76 and at a preferred angle of about 30 degrees from the longitudinal axis of the catheter 60.

The side opening 58 also includes distal and proximal ends 78 and 80 which are spaced apart from each other and extend between the first and second sides 74 and 76 to form an elongated slot-shaped member in the sidewall of the catheter 60. As with the prior embodiment and described more fully above, the angles formed between the ends and sides of the side opening are optimized to facilitate the operational characteristics of the catheter 60 during its insertion, use and removal. The side opening 58 in this embodiment is preferably about 1.3 inches from the distal end of the catheter. The side opening 82 for the third lumen 68 is located about midway between the side opening 58 and the distal end of the catheter. The side opening 82 of this embodiment is preferably a conventional hole although an elongated slot-shaped opening which may extend about 40 degrees around the circumference of the catheter 60 between the intersection of the ends of the second wall portion 72 with the sidewall of the catheter 60 may also be used. A slot-shaped side opening 82 would be preferably diagonally oriented along the sidewall of the catheter and include first and second ends and distal and proximal sides which would be similar to those described above with respect to side openings 30 and 58. The slot-shaped side opening 58 is preferably laser cut into the sidewall of the catheter 60 although, due to the relative size of side opening 82, this side opening 82 may be punched or otherwise formed as a round or otherwise shaped opening without significantly affecting the performance of the present embodiment.

Figure 15:
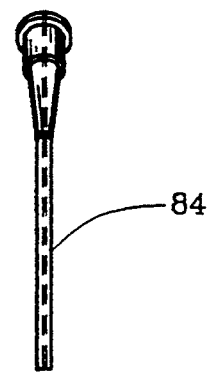
FIG. 15 is an elevated side view of a single lumen catheter constructed in accordance with the present invention.

FIG. 15 shows a further embodiment of the present invention wherein a single lumen catheter 84 preferably includes at least one generally slot-shaped side opening 86 thereon. In the preferred form of this embodiment, the side opening 86 extends about 180 degrees around the circumference of the catheter 84 and is diagonally oriented with respect to the longitudinal axis of the catheter 84 at a preferred angle of approximately 30 degrees. In this embodiment, the lumen of the catheter 84 is preferably open at the distal end of the catheter although the lumen may be closed distally of the side opening 86 depending on the intended use of the catheter. The side opening of the single lumen catheter preferably includes first and second sides as well as distal and proximal ends, the features of which are more fully described above with respect to the side opening 30 of the preferred embodiment. In this embodiment, the side opening 86 functions as an overflow opening if the opening on the distal end of the catheter is obstructed or provides resistance to the flow of fluid therethrough. If there is no opening on the distal end of the catheter, the side opening 86 will function in a manner similar to the side openings described above.

Figure 16:
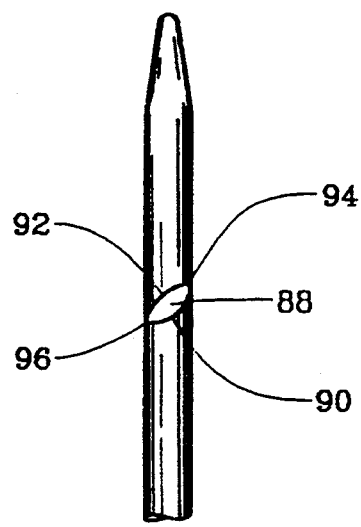
FIG. 16 is an elevated side view of an alternate form of the side opening of the present invention.

FIG. 16 illustrates a further alternate embodiment wherein the side opening 88 is generally elliptically shaped. In this embodiment, the side opening 88 includes a proximally located first side 90 and a distally located second side 92. As shown in FIG. 16, the side opening also includes distal and proximal ends 94 and 96, respectively, which are located at the respective intersections of the first and second sides, 90 and 92.

This embodiment is illustrative that the sides 90 and 92 of the side opening 88 need not be straight as described above. It is anticipated that the side opening 88 may have a shape similar to a lanceolate ellipse where each side may be elliptically or semicircularly shaped wherein the elliptical or semicircular sides are parallel to each other or oppositely facing each other generally as shown in FIG. 16.

While the foregoing description has been drawn to the presently preferred embodiments of the present invention, it should be understood by those skilled in the art of the present subject matter that various modifications may be made to the present invention without departing from the scope and spirit of the invention which is defined by the following claims.

What is claimed is:

1. An elongate catheter comprising:
    an elongate body portion formed by a circumferential sidewall and having a longitudinal axis and distal and proximal end portions thereon;
    a first lumen in said body portion extending between said proximal end portion and a side opening formed in said sidewall of said body portion;
    said side opening including first and second sides thereon wherein said first side is formed proximally of said second side on said sidewall, a plurality of spaced apart ends extending between said first and second sides such that at least one of said first and second sides is oriented diagonally with respect to said longitudinal axis of said body portion; and
    wherein said body portion includes a plurality of lumens therein formed by a septum extending longitudinally along said body portion, and a second lumen extends between an opening on said distal end portion and said proximal end portion.

2. The catheter of claim 1 wherein said ends form distally and proximally positioned ends on said side opening between said first and second sides such that said side opening is generally slot-shaped.

3. The catheter of claim 2 wherein said distally and proximally positioned ends are oriented generally parallel to each other.

4. The catheter of claim 2 wherein said body portion includes a plurality of lumens therein formed by a septum extending therethrough, and said first and second sides of said side opening are generally parallel to each other.

5. The catheter of claim 1 wherein at least one of said lumens is generally D-shaped in cross section and said D-shaped lumen is in flow communication with said side opening along said distal end portion of said body portion.

6. The catheter of claim 5 wherein said septum intersects said sidewall of said body portion in at least first and second locations and said first end of said side opening is generally adjacent to said first location.

7. The catheter of claim 6 wherein said second end is generally adjacent to said second location.

8. The catheter of claim 1 wherein said septum is formed of first and second wall portions, and said second wall portion includes first and second ends which intersect said sidewall of said body portion.

9. The catheter of claim 8 wherein said side opening communicates with at least one of said lumens and said first end of said side opening is adjacent to said first wall portion, and said second end of said side opening is adjacent to said second wall portion of said septum.

10. The catheter of claim 8 wherein said side opening communicates with at least one of said lumens, and said end walls of said side opening are adjacent said first and second ends of said second wall portion.

11. The catheter of claim 8 wherein said second wall portion of said septum is generally semicircularly shaped.

12. The catheter of claim 8 wherein said second wall portion of said septum is generally bent.

13. The catheter of claim 1 wherein said spaced apart ends include distal and proximal wall portions thereon, and the intersection of said distal wall portion and second side of said side opening is located distally of the intersection of said proximal wall portion and said first side of said side opening.

14. The catheter of claim 1 wherein said spaced apart ends include distal and proximal wall portions thereon, and the intersection of said distal wall portion and said first side of said side opening is located proximally of the intersection of said proximal wall portion and said second side of said side opening.

15. The catheter of claim 1 wherein said spaced apart ends include distal and proximal wall portions thereon, and the intersection of said distal wall portion and said first side of said side opening is located distally of the intersection of said proximal wall portion and said first side of said side opening.

16. The catheter of claim 1 wherein said spaced apart ends include distal and proximal wall portions thereon, and the angle formed by the intersection of said first side of said side opening and said distal wall portion is greater than the angle formed by the intersection of said first side of said side opening and said proximal wall portion.

17. The catheter of claim 1 wherein said spaced apart sidewalls include distal and proximal wall portions thereon, and the angle formed by the intersection of said second side of said side opening and said distal wall portion is less than the angle formed by the intersection of said second side of said side opening and said proximal wall portion.

18. The catheter of claim 1 wherein said side opening extends greater than 40 degrees around the circumference of said body portion.

19. The catheter of claim 1 wherein said first and second sides of said side opening are not perpendicular to said longitudinal axis of said body portion.

20. The catheter of claim 1 wherein said ends of said side opening are generally parallel to said longitudinal axis of said body portion.

21. An elongate catheter comprising:
    an elongate body portion formed by a circumferential sidewall having a longitudinal axis and distal and proximal end portions;
    a plurality of lumens in said body portion and at least one of said lumens extending between said proximal end portion and a generally elongate side opening formed in said sidewall of said body portion; and
    said side opening including distal and proximal side portions and at least one of said distal and proximal side portions are oriented diagonally with respect to said longitudinal axis of said body portion.

22. The catheter of claim 21 wherein said side opening further includes first and second ends thereon, and said first and second ends each intersect said distal and proximal side portions to form a generally slot-shaped side opening.

23. The catheter of claim 21 further including a distal opening on the distal end of said distal end portion wherein said distal opening is in flow communication with a first lumen of said body portion and said side opening is in flow communication with a second lumen of said body portion.

24. The catheter of claim 23 further including a third lumen in said body portion and said third lumen is in flow communication with a further side opening in said sidewall of said body portion.

25. The catheter of claim 21 wherein said distal and proximal side portions of said side opening are oriented generally parallel to each other.

26. An elongate catheter comprising:
an elongate body portion formed by a circumferential sidewall having a longitudinal axis and distal and proximal end portions;
a plurality of lumens in said body portion and at least one of said lumens extending between said proximal end portion of said body portion and a generally elongate side opening formed in said sidewall of said body portion; and
said side opening including distal and proximal ends and first and second sides wherein said first side is formed proximally of said second side of said side opening on said sidewall, and said distal and proximal ends are oriented generally parallel to each other, and said side opening is oriented generally diagonally to said longitudinal axis of said body portion.

27. A method of inserting a catheter into a patient comprising:
forming an elongate catheter having a side opening therein wherein the side opening is oriented generally diagonal with respect to the longitudinal axis and includes distally and proximally located ends thereon, and
inserting the catheter into an incision of the patient with a rotational movement along the orientation of the side opening.

28. The method of claim 27 wherein the catheter is rotated so that the distally located end of the side opening contacts the tissue prior to the proximally located end of the side opening so that the catheter is threaded into the incision.

* * * * *